US00PP29509P2

(12) United States Plant Patent
Hansen

(10) Patent No.: US PP29,509 P2
(45) Date of Patent: Jul. 17, 2018

(54) ***LAGERSTROEMIA* PLANT NAMED 'BUBBLE TEA'**

(50) Latin Name: ***Lagerstroemia* (L.) hybrid**
Varietal Denomination: Bubble Tea

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 36 days.

(21) Appl. No.: 15/530,531

(22) Filed: Jan. 25, 2017

(51) Int. Cl.
*A01H 5/00* (2018.01)

(52) U.S. Cl.
USPC ..... Plt./252

(58) Field of Classification Search
USPC ..... Plt./226, 252
See application file for complete search history.

(56) References Cited

PUBLICATIONS

Walters Garden's 2016-2017 Catalogue. https://www.provenwinners.com/sites/provenwinners.com/files/catalogs_pdfs/1-26_front_pages.pdf. 5 pages.*

* cited by examiner

*Primary Examiner* — Susan McCormick Ewoldt
*Assistant Examiner* — Karen M Redden

(57) ABSTRACT

The new and distinct crape myrtle plant named *Lagerstroemia* 'Bubble Tea' has a dense, compact, rounded habit, is ground hardy to at least USDA zone 6, has deep green foliage slowly that emerges with a blush of burgundy. The flowers arise from shiny red buds, are fragrant, large, completely cover the shrub with their lilac-purple color. The new plant resists leaf spot and powdery mildew and is useful in the landscape as a specimen, en masse, or as a container plant.

1 Drawing Sheet

Botanical classification: *Lagerstroemia* (L.) hybrid.
Variety denomination: 'Bubble Tea'.

BACKGROUND OF THE INVENTION

The present invention relates to a new and distinct cultivar of *Lagerstroemia* plant, commonly known as crape myrtle, and hereinafter referred to by the cultivar name 'Bubble Tea' or the "new plant." 'Bubble Tea' is grown primarily as an ornamental for landscape use and for use as a potted plant and is the result of an ongoing breeding program to produce new and improved garden worthy plants for the ornamental market. The new plant was the result of open-pollinated seed collected by the inventor in fall of 2010 at a cultivated landscape in Raleigh, N.C., USA using 'Whit VI' U.S. Plant Pat. No. 14,438 also known as 'Burgundy Cotton' as the seed or female parent. The male or pollen parent is unknown, but may have been any one of a number of hybrids or cultivars in the breeding area.

No plants of *Lagerstroemia* 'Bubble Tea' have been sold, in this country or anywhere in the world, prior to the filing of this application, nor has any disclosure of the new plant been made prior to the filing of this application with the exception of that which may have been disclosed or sold within one year of the filing of this application and was either derived directly or indirectly from the inventor.

*Lagerstroemia* 'Bubble Tea' was initially asexually propagated by stem cuttings at a wholesale perennial nursery in Zeeland, Mich., USA in 2012. The resultant plants from successive generations have demonstrated that the new plant has remained stable and true to type in multiple generations of asexual propagation.

SUMMARY OF THE INVENTION

Plants of the new cultivar 'Bubble Tea' have not been observed under all possible environmental conditions. The phenotype may vary somewhat with changes in light, temperature, soil and available moisture and fertility without, however, any variance in genotype.

The following traits have been repeatedly observed and are determined to be unique characteristics of 'Bubble Tea'. Among the characteristics in combination which distinguish 'Bubble Tea' as a new and distinct cultivar, unique from all other cultivars known to the inventor are:

1. Dense, compact, rounded growth habit;
2. Semi-glossy foliage of deep green with light burgundy blush as developing;
3. Heavily-branched reddish-colored stems;
4. Bright lilac-purple flowers open from shiny red buds to completely cover the shrub;
5. Resistance to *Cercospora* leaf spot and *Erisphe* powdery mildew;
6. Ground hardy to at least USDA hardiness zone 6.

'Bubble Tea' is distinguished from its female parent with flowers that are bright lilac-purple and a more compact rounded habit. The most similar cultivars known to the inventor include: 'Catawba' (not patented), 'Spiced Plum' co-pending U.S. Plant patent application Ser. No. 15/530,535, 'Sweet Macchiato' U.S. Plant Pat. No. 28,759 and 'Whitt VI' U.S. Plant Pat. No. 14,438. 'Catawba' is much taller in habit and has flowers of more purple. 'Spiced Plum' has a smaller habit and the flowers are more raspberry-purple. 'Sweet Macchiato' has similar habit, but the flowers are more hot pink and the foliage has a deeper and more intense burgundy tinting. 'Whitt VI' is much larger in habit and has flowers of more white than the new plant.

BRIEF DESCRIPTION OF THE DRAWINGS

The accompanying color photographs illustrate the flower and foliage characteristics and the overall appearance of 'Bubble Tea', showing the colors as true as it is reasonably possible to obtain in color reproductions of this type. Colors in the photographs may differ slightly from the color values cited in the detailed botanical description which accurately describe the colors of the new *Lagerstroemia*.

DETAILED BOTANICAL DESCRIPTION

Figure 1:
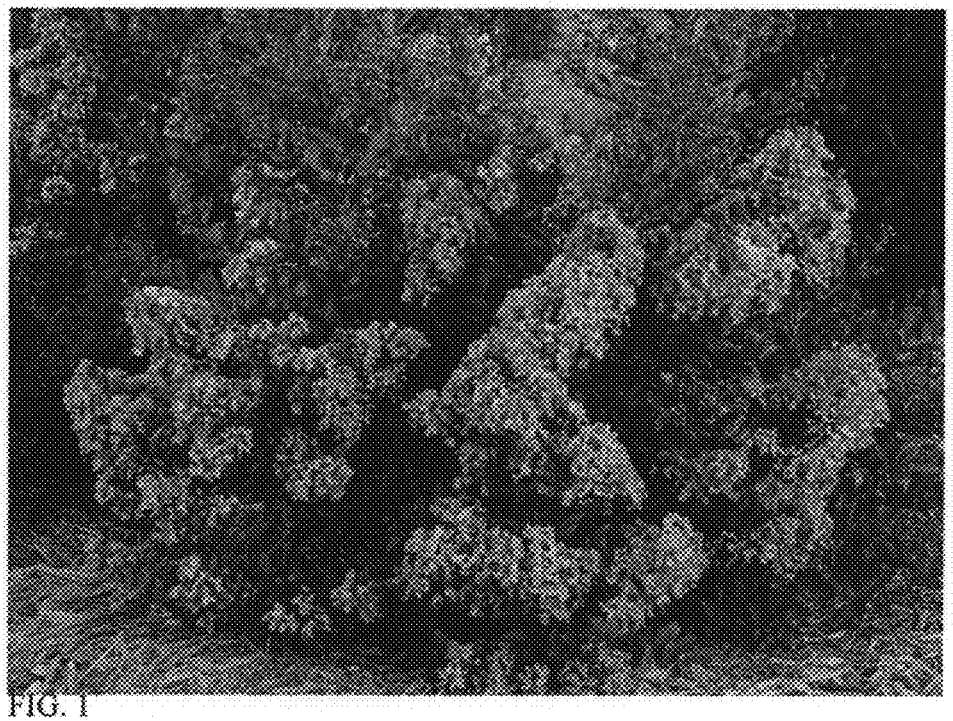
FIG. 1 shows a four-year-old plant in a landscape in late summer peak flowering.
Figure 2:
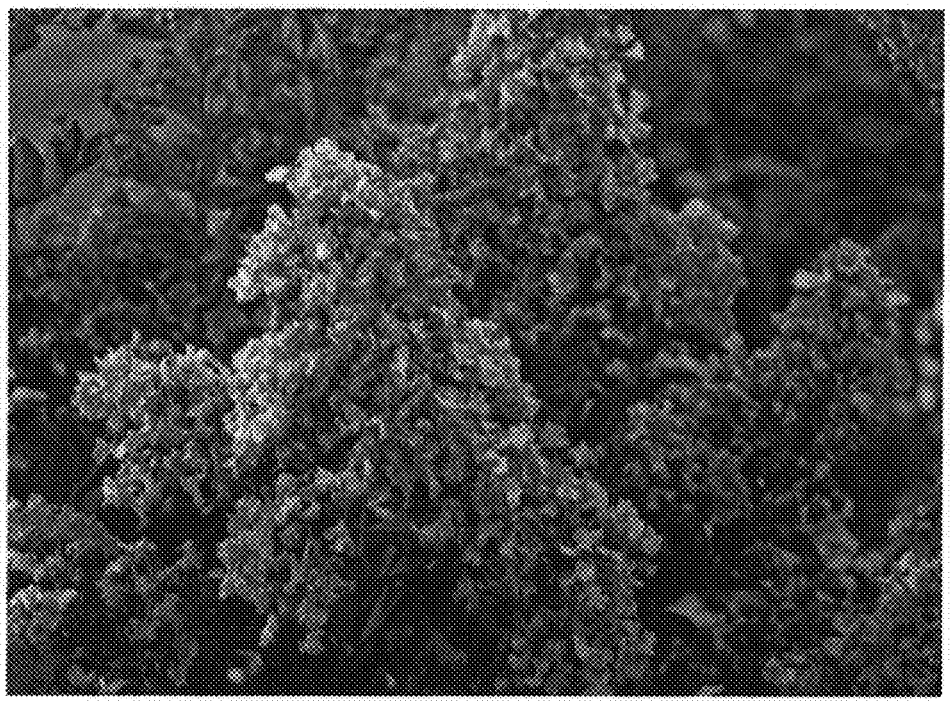
FIG. 2 shows a close-up for the flowers and buds.

The following color references are based on the 2001 edition of The Royal Horticultural Society Colour Chart except where common dictionary terms are used. The following observations and size descriptions are of approximately four-year-old plants grown in a loamy-sand, full-sun, open trial bed in Zeeland, Mich., USA with supplemental water and fertilizer as needed. The phenotype may vary slightly with different environmental conditions, such as temperature, light, fertility, moisture and maturity levels, but without any change in the genotype.

Botanical classification: *Lagerstroemia* L.;

Parentage: Female, or seed parent 'Whit VI'; the male, or pollen parent is unknown (open-pollinated);

Propagation: Terminal softwood stem cuttings;

Time to initiate roots: About three weeks;

Growth rate: Moderate; about 10 weeks to finish and flower in a 3.7 liter container from a 65 mm liner;

Plant description: Deciduous, woody, narrow, compact flowering shrub; about six mainly upright to outward primary stems; freely branched;

Root description: Fine, numerous, fibrous, well-branched;

Plant habit: About 110 cm high from the soil level to the top of the inflorescences; about 134 cm wide with no pinching, pruning or plant growth regulators;

Stems: To about 110.0 cm long and about 14.0 mm diameter at base, terete; young stems terete and four longitudinal carinae, along line on either side of petioles;

Stem color: Woody basal 15 cm of blend between RHS 156D and RHS 165D with exfoliating striations of closer to RHS 165B than RHS 165A; young developing stems striated with a blend between RHS 165A and RHS 165B and a blend between RHS 166A and RHS 166B;

Node: About 22 to 28 per main stem; internode length average about 3.2 cm in main stems;

Node color: Same as surrounding stem;

Foliage description: Sub-opposite to alternate; simple; oval; margin ciliolate, slightly involute; acute apex; rounded to attenuate base; average about 4.3 cm long and 2.4 cm wide; adaxial and abaxial glabrous and lustrous;

Abaxial leaf color: Young emerging leaf nearest RHS 148A with blush of nearest RHS 183B; mature leaf nearest RHS 137A;

Adaxial leaf color: Young emerging foliage between RHS 148A and RHS 147A with slight blush of nearest RHS 187A; mature leaf between RHS 146A and RHS 146B;

Adaxial and abaxial ciliate margin color: Nearest RHS 187B throughout most of season;

Veins: Pinnate, puberulent adaxial and abaxial;

Vein color: Young emerging leaf adaxial midrib base between RHS 187B and RHS 187C with distal base and lateral veins nearest RHS 183C; young emerging leaf abaxial midrib and lateral veins nearest RHS 187C; mature adaxial midribs and lateral veins nearest RHS 147C blushed at midrib base with nearest RHS 187A; mature abaxial midrib between RHS N170C and RHS N170D and lateral veins nearest RHS 147D with blush of nearest RHS N170C;

Petiole: Short to sessile; adaxial puberulent, slightly puberulent abaxial; slightly applanate adaxial; about 1.0 mm long and 2.0 mm across;

Petiole color: Young adaxial nearest RHS 187B, young abaxial nearest RHS 187C; mature adaxial nearest RHS 147C and abaxial nearest RHS N170C;

Inflorescence: Panicle; terminal branched panicles up to about 400 flowers; average about 300 flowers; up to about 75.0 cm long and about 44.0 cm across; beginning late-summer and continuing until fall, for about eight weeks;

Buds: Globose with rounded to slightly cuspidate apex and rounded base; laevigate; glabrous; about 9.0 mm tall and about 8.0 mm diameter one day prior to opening;

Bud color: Nearest RHS 53B;

Flowers: Perfect; regular; actinomorphic; terminal panicle; individually about 2.5 cm across and about 20.0 mm tall; lasting about two days;

Flower fragrance: Sweet, light;

Peduncle: Terete with four longitudinal carinae in basal portion and rounded in distal portion; about 5.5 mm diameter at base below lowest flowering branch, to about 75.0 cm long;

Peduncle color: Variable with position; proximal nearest RHS between RHS 165A and RHS 165B and distal portion nearest RHS 183C;

Pedicel: Terete, about 6.0 trim long and 1.0 mm diameter;

Pedicel color: Between RHS 187C and RHS 183C;

Sepals: Fused in about the basal 4.0 mm; acute apex, entire margin; glabrous and laevigate both adaxial and abaxial; about 8.0 mm long and individually about 4.0 mm long above the fusion and about 3.0 mm wide at fusion point;

Sepal color: Adaxial basal 5.0 mm lighter than RHS 145D, distal 3.0 mm nearest RHS 183B; abaxial basal 5.0 mm nearest RHS 184C, distally nearest RHS 183B; adaxial basal 5.5 mm nearest RHS 150D, portion below apex nearest RHS 184B and apex between RHS 194C and RHS 194D; abaxial basal 5.5 mm nearest RHS 145B, portion below apex nearest RHS 183B and apex nearest RHS 181B;

Petals: Six; stalked; glabrous; blade ruffled or crisped; margin crisped; blade with rounded apex and cordate to sagittate base, to about 12.0 mm across and 13.0 mm long; claw base adnate to calyx, to about 6.0 mm long and 0.5 mm diameter; overall about 1.8 cm long; blade to about 9.0 mm long and about 12.0 mm across;

Petal color: Blade adaxial and abaxial blend between RHS N74D and RHS N80C; claw nearest RHS 53C;

Androecium:

*Stamens*.—Typically about 36; six longer and about 30 shorter.

*Filaments*.—Longer stamens to about 15.0 mm long and about 0.5 mm diameter, curled about 90 to 180 degrees in distal 5.0 mm; shorter filaments about 9.0 mm long and less than 0.3 mm diameter; color of longer filaments nearest RHS 53C.

*Anthers*.—Flattened ellipsoid; more developed on longer stamens to about 1.2 mm long and 1.0 mm across, on shorter stamens about 1.0 mm long and about 0.7 mm across; color nearest RHS N170C.

*Pollen*.—Abundant on longer stamens; color nearest RHS 13B.

Gynoecium: One;

*Style*.—Terete; glabrous; about 19.0 mm long and 1.0 mm diameter; color nearest RHS 53B in the middle portion, distally nearest RHS 53A and base nearest RHS 53B.

*Stigma*.—Globose; about 1.1 mm diameter; color nearest RHS 182B.

*Ovary*.—Superior; globose; about 2.0 mm tall and 2.0 mm diameter; color nearest RHS 150D.

Fruit: Globose; glabrous; six-valved dehiscent capsule; about 7.0 mm wide and 7.0 mm tall; apex rostrate to rounded; base rounded;

Fruit color: Between RHS 165B and RHS 165A;

Seed: Samara; lunate; about 6.0 mm long and 2.0 mm across at widest point and 1.0 mm thick at embryo;

Seed color: Nearest RHS 199B at embryo end and lighter than RHS 199D at distal end;

Disease resistance: *Lagerstroemia* 'Bubble Tea' has shown resistance to powdery mildew and black leaf spot, *Erisphe* and *Cercospora* fungi, respectively. Other resistance beyond that typical for crape myrtle has not been observed. The new plant's root system is capable of withstanding cold temperatures typical of those found in USDA zone 6.

It is claimed:

1. A new and distinct cultivar of crape myrtle plant named *Lagerstroemia* 'Bubble Tea' essentially as herein illustrated and described.

* * * * *